US012575976B2

(12) United States Patent
De et al.

(10) Patent No.: US 12,575,976 B2
(45) Date of Patent: Mar. 17, 2026

(54) URINE QUANTIFYING BED PAD

(71) Applicant: Recker Medical, Arlington, VA (US)

(72) Inventors: Bianca De, San Ramon, CA (US); Ian Christman, Buffalo, NY (US); Jillian Gallagher, Boston, MA (US); Brian Kolich, Aliquippa, PA (US); Yajnesh Vedanaparti, Philadelphia, PA (US); Toby Shen Zhu, Wildwood, MO (US)

(73) Assignee: Recker Medical, Arlington, VA (US)

( * ) Notice: Subject to any disclaimer, the term of this patent is extended or adjusted under 35 U.S.C. 154(b) by 488 days.

(21) Appl. No.: 18/053,179

(22) Filed: Nov. 7, 2022

(65) Prior Publication Data

US 2023/0141612 A1     May 11, 2023

Related U.S. Application Data

(60) Provisional application No. 63/276,820, filed on Nov. 8, 2021.

(51) Int. Cl.
*A61F 13/15*         (2006.01)
*A61F 13/51*         (2006.01)
(Continued)

(52) U.S. Cl.
CPC .................. *A61F 13/15203* (2013.01); *A61F 2013/15463* (2013.01); *A61F 2013/5103* (2013.01);
(Continued)

(58) Field of Classification Search
CPC .. A61F 13/42; A61F 13/00; A61F 5/48; A61F 5/44; A61F 13/15; A61F 13/51;
(Continued)

(56) References Cited

U.S. PATENT DOCUMENTS 4,231,370 A * 11/1980 Mroz ..................... A61F 13/42
                                                    604/389
6,284,942 B1    9/2001 Rabin
                    (Continued)

FOREIGN PATENT DOCUMENTS

WO          2020/257053    * 12/2020 ............. A61F 13/00
WO      WO-2023/081445       5/2023

OTHER PUBLICATIONS

International Search Report and Written Opinion for International Application No. PCT/US22/49097 dated Feb. 21, 2023.

*Primary Examiner* — Michele Kidwell
(74) *Attorney, Agent, or Firm* — Stephen J. Kenny; Nicole A. Bustos-Pomerantz; Foley Hoag LLP

(57)          ABSTRACT

An absorbent pad including a top layer. The top layer including a first sheet, the first sheet including an outward face and an inward face, wherein the first sheet comprises a wicking material, the first sheet further including a volume approximation grid having a plurality of fluid volume estimation regions. The top layer including a second sheet, the second sheet comprising an absorbent material, the second sheet attached to the inward face of the first sheet. The absorbent pad including a bottom layer including an outward face and an inward face, the inward face of the bottom layer attached to the second sheet. The absorbent pad including a visual fluid indicator disposed on at least a portion of the top layer or the bottom layer.

20 Claims, 10 Drawing Sheets

(51) Int. Cl.
    *A61F 13/53*            (2006.01)
    *A61F 13/534*           (2006.01)

(52) U.S. Cl.
    CPC ............. *A61F 2013/530299* (2013.01); *A61F 2013/53062* (2013.01); *A61F 2013/53445* (2013.01)

(58) Field of Classification Search
    CPC .......... A61B 5/00; A61B 5/204; A61B 5/202; B41F 21/00; B41M 5/00; D06P 5/30; G01N 21/77; G01N 21/78; G01N 31/22; A01K 1/015; A47C 21/06; A61G 7/057
    USPC ......................................................... 604/361
    See application file for complete search history.

(56)                    References Cited

U.S. PATENT DOCUMENTS

| | | | | |
|---|---|---|---|---|
| 2002/0062114 | A1* | 5/2002 | Murai | A61F 13/84 604/385.01 |
| 2004/0055367 | A1* | 3/2004 | Swiecicki | A61F 13/42 73/73 |
| 2012/0238977 | A1* | 9/2012 | Oku | A61F 13/15707 604/361 |
| 2013/0116646 | A1 | 5/2013 | Robles | |
| 2018/0008494 | A1 | 1/2018 | Li | |
| 2020/0214898 | A1* | 7/2020 | Waite | A61F 13/01029 |
| 2023/0141612 | A1 | 5/2023 | De et al. | |
| 2023/0146455 | A1 | 5/2023 | Yu et al. | |

* cited by examiner

102a

102b

URINE QUANTIFYING BED PAD

CROSS-REFERENCE TO RELATED APPLICATIONS

This application claims the benefit of priority to U.S. Provisional Patent Application No. 63/276820, filed on Nov. 8, 2021, the entirety of which is incorporated herein by reference.

FIELD OF THE INVENTION

Embodiments of the present disclosure generally relate to fluid (e.g., urine) absorbent pads having visual fluid indicators for quantifying fluid presence and approximating fluid volume.

BACKGROUND

Monitoring fluid balance in the human body is of vital clinical importance, as fluid balance is used for monitoring disease status, for drug titration, and for guiding clinical decision making. Lack of fluid balance can result in dehydration or over-hydration, each of which can cause health issues. For example, overhydration (where in>out) may lead to seizures, edema, and/or brain swelling. In another example, dehydration (where in<out) may result in seizures, shock, and or kidney failure, among other things.

While fluid intake is easily measured, tracking fluid output remains a challenge in certain patient demographics. When strict input and outputs (I&Os) are necessary, continent patients urinate into a pan in the toilet. However, over 50% of Americans over the age of 65 are affected by some form of incontinence. For these patients, clinicians use utilize an indwelling catheter (e.g., Foley catheter) that directly drains fluid from the bladder. Catheterization is widely known to lead to increased risk of nosocomial complications such as urinary tract infections, blood infections, urethral damage, soft tissue breakdown, and sepsis, in addition to being extremely uncomfortable for patients. For incontinent patients who do not require strict I&Os, absorbent bed pads are placed under them to catch urine but are unable to measure fluid output. While weighing pads to estimate volume is technically possible and is performed in the pediatric population, for the majority of adult inpatient services this is impractical and not clinically feasible.

Accordingly, there is a need for an absorbent bed pad that can accurately estimate urine output to thereby reduce the use of catheters (e.g., Foley catheters) in certain incontinent patients as well as provide fluid output data that can be used to guide clinical decision making.

BRIEF SUMMARY

The purpose and advantages of the disclosed subject matter will be set forth in and apparent from the description that follows, as well as will be learned by practice of the disclosed subject matter. Additional advantages of the disclosed subject matter will be realized and attained by the methods and systems particularly pointed out in the written description and claims hereof, as well as from the appended drawings.

To achieve these and other advantages and in accordance with the purpose of the disclosed subject matter, as embodied and broadly described, the disclosed subject matter includes an absorbent pad including a top layer including a first sheet. The first sheet including an outward face and an inward face, wherein the first sheet includes a wicking material, the first sheet further including a volume approximation grid having a plurality of fluid volume estimation regions and a second sheet, the second sheet including an absorbent material. The second sheet attached to the inward face of the first sheet. The absorbent pad including a bottom layer including an outward face and an inward face, the inward face of the bottom layer attached to the second sheet. The absorbent pad including a visual fluid indicator disposed on at least a portion of the top layer or the bottom layer.

The disclosed subject matter also includes a method of detecting the presence of and approximating a volume of a fluid, the method including providing an absorbent pad, the absorbent pad including a top layer including a first sheet. The first sheet including an outward face and an inward face, wherein the first sheet includes a wicking material, the first sheet further including a volume approximation grid having a plurality of fluid volume estimation regions. The top layer including a second sheet, the second sheet including an absorbent material, the second sheet attached to the inward face of the first sheet. The absorbent pad including a bottom layer having an outward face and an inward face, the inward face of the bottom layer attached to the second sheet. The absorbent pad including a visual fluid indicator disposed on at least a portion of the top layer or the bottom layer. The method including contacting the absorbent pad with the fluid and determining a number of regions on the first sheet having the fluid thereon.

The disclosed subject matter also includes a method of manufacturing an absorbent pad, the method includes providing a top layer comprising a first sheet and a second sheet, the first sheet having an outward face and an inward face, the second sheet attached to the inward face of the first sheet, wherein the first sheet comprises a wicking material, wherein the second sheet comprising an absorbent material. The method includes providing a bottom layer comprising an outward face and an inward face. The method includes forming a volume approximation grid having a plurality of fluid volume estimation regions on at least a portion of the first sheet. The method includes applying a visual fluid indicator on one or both of the top layer and the bottom layer. The method includes affixing the top layer or the bottom layer having the visual fluid indicator applied thereon to the top layer or the bottom layer.

It is to be understood that both the foregoing general description and the following detailed description are exemplary and are intended to provide further explanation of the disclosed subject matter claimed.

The accompanying drawings, which are incorporated in and constitute part of this specification, are included to illustrate and provide a further understanding of the method and system of the disclosed subject matter. Together with the description, the drawings serve to explain the principles of the disclosed subject matter.

BRIEF DESCRIPTION OF THE SEVERAL VIEWS OF THE DRAWINGS

A detailed description of various aspects, features, and embodiments of the subject matter described herein is provided with reference to the accompanying drawings, which are briefly described below. The drawings are illustrative and are not necessarily drawn to scale, with some components and features being exaggerated for clarity. The drawings illustrate various aspects and features of the present subject matter and may illustrate one or more embodiment(s) or example(s) of the present subject matter in whole or in part.

DETAILED DESCRIPTION

Reference will now be made in detail to exemplary embodiments of the disclosed subject matter, an example of which is illustrated in the accompanying drawings. The method and corresponding steps of the disclosed subject matter will be described in conjunction with the detailed description of the system.

Figure 1:
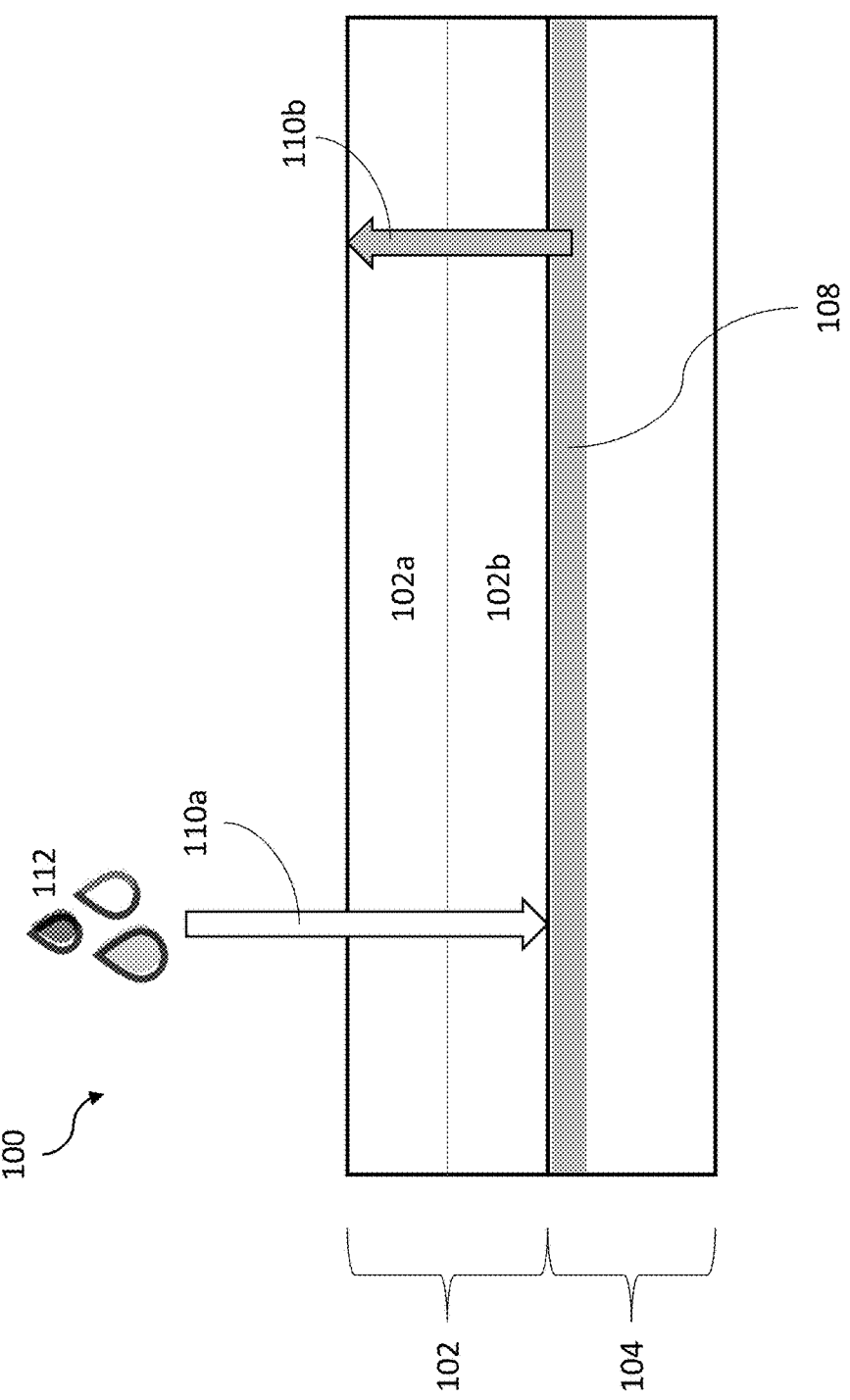
FIG. 1 illustrates an absorbent pad in accordance with an embodiment of the present disclosure.

The methods and systems presented herein may be used for non-invasively using ultrasonic energy to repair degenerated intervertebral discs. The disclosed subject matter is particularly suited for outpatient systems and methods for non-invasively using ultrasonic energy on a target area of a patient's body, the target area corresponding to degenerated intervertebral discs. For purpose of explanation and illustration, and not limitation, an exemplary embodiment of the system in accordance with the disclosed subject matter is shown in FIG. 1 and is designated generally by reference character 100. Similar reference numerals (differentiated by the leading numeral) may be provided among the various views and Figures presented herein to denote functionally corresponding, but not necessarily identical structures.

In general, as shown in FIG. 1, an absorbent pad 100 of the present disclosure includes at least one top layer 102 configured to absorb a fluid (e.g., urine) and at least one bottom layer 104, one of the top and/or bottom layer having a visual fluid indicator of a fluid. In various embodiments, the bottom layer 104 may be configured to absorb fluid alternatively or additionally to the top layer 102. In various embodiments, the top layer 102 is configured to wick and/or absorb the fluid (e.g., urine). In various embodiments, the visual fluid indicator is disposed within at least a portion of the bottom layer 104. In various embodiments, the visual fluid indicator is disposed within at least a portion of the top layer 102. In various embodiments, the top layer 102 may include one or more sheets sandwiched together; each top layer can be of a coextensive size/shape, or be formed with varying dimensions as desired. In various embodiments, a first sheet 102a of the top layer 102 includes a side facing outwardly (i.e., towards the patient) and includes a wicking material configured to allow the fluid to wick across the first sheet 102a. In various embodiments, the wicking material may include cotton fibers. In various embodiments, the wicking material may include synthetic (e.g., polymer) fibers. In various embodiments, the wicking material may include at least one of: cellulose fibers, woven mesh, glass fibers, polyester, and/or nylon. In various embodiments, the first sheet 102a may include any suitable thickness to wick the fluid at a predetermined rate (e.g., speed of fluid movement across a material). In various embodiments, the thickness of the first sheet 102a may be dependent on the particular use-case. In various embodiments, the wicking sublayer includes a soft, porous polyester, which allows for fluid spread and then absorption by the lower layer(s). In various embodiments, a separate component formed as a sheet in and of itself, the sheet soaked with a visual fluid indicator, such as a dye as described herein, may be inserted into any one of the top layer 102, bottom layer 104, or a combination thereof.

In various embodiments, the top layer 102 further includes a second sheet 102b (below the first sheet 102a) having an absorbent material configured to absorb the fluid, in embodiments. In various embodiments, the second sheet 102b may include cotton. In various embodiments, the cotton may be combined with an additional absorbent material. In various embodiments, the second sheet 102b may include any suitable thickness to absorb a predetermined amount of fluid. For example, a thicker sheet may be used where more absorption is required (e.g., an adult pad). In another example, a thinner sheet may be used where less absorption is required (e.g., a pediatric pad). In various embodiments, the thickness, size, absorbance, dye-infusion or other factors may be controlled by the insertion and removal of one or more sheets. For example, a sheet having a desired absorbance may be inserted into one or more receptacles disposed between or formed by the first and second sheets 102a, 102b. In various embodiments, the thickness of the second sheet 102b may be dependent on the particular use-case. In various embodiments, the top layer 102 may include two or more (e.g., three, four, five, etc.) sheets configured to absorb fluid. For example, in situations where a relatively large amount of fluid will be absorbed (e.g., an adult pad), the second sheet 102b may include two or more absorbent sheets, in various embodiments. In another example, in situations where relatively less fluid will be absorbed (e.g., a pediatric pad), the second sheet 102b may include a single absorbent sheet or an absorbent sheet configured for pediatric use, varying its thickness and planform size, for example. In various embodiments, the absorbent material may include an absorbent polymer (e.g., hydrophilic polymer). The absorbent can include a catalyst that imparts a phase change to the bodily fluid, converting the fluid into a solid, gel, or other more viscous state/consistency. In various embodiments, the absorbent material absorbs between 1 and 100 times its mass in fluid. In various embodiments, the absorbent material absorbs more than 100 times its mass in fluid. In various embodiments, the absorbent material absorbs more than 1000 times its mass in fluid. In various embodiments, the absorbent material absorbs between 100 and 1000 times its mass in fluid. In various embodiments, the absorbent polymer includes sodium polyacrylate. In various embodiments, the absorbent polymer may be dispersed within the fibers (e.g., cotton fibers) of the second sheet. In various embodiments, the absorbent material may include at least one of: sodium polyacrylate, polyacrylamide copolymer, ethylene maleic anhydride copolymer, cross-linked carboxymethylcellulose, polyvinyl alcohol copolymers, cross-linked polyethylene oxide, and starch grafted copolymer of polyacrylonitrile. In various embodiments, the absorbent material may be integrated into the sheet. In various embodiments, the absorbent material may be dispersed within cotton fibers.

In various embodiments, the absorbent material may be distributed evenly across the top layer or any layer on which it is disposed or forms at least a part. For example, an absorbent polymer (e.g., sodium polyacrylate) may be evenly distributed throughout a cotton layer. In various embodiments, the absorbent material may not be uniformly distributed throughout the top layer. For example, the absorbent material may be concentrated at the centers of each fluid volume estimation region in the grid pattern.

Figure 2:
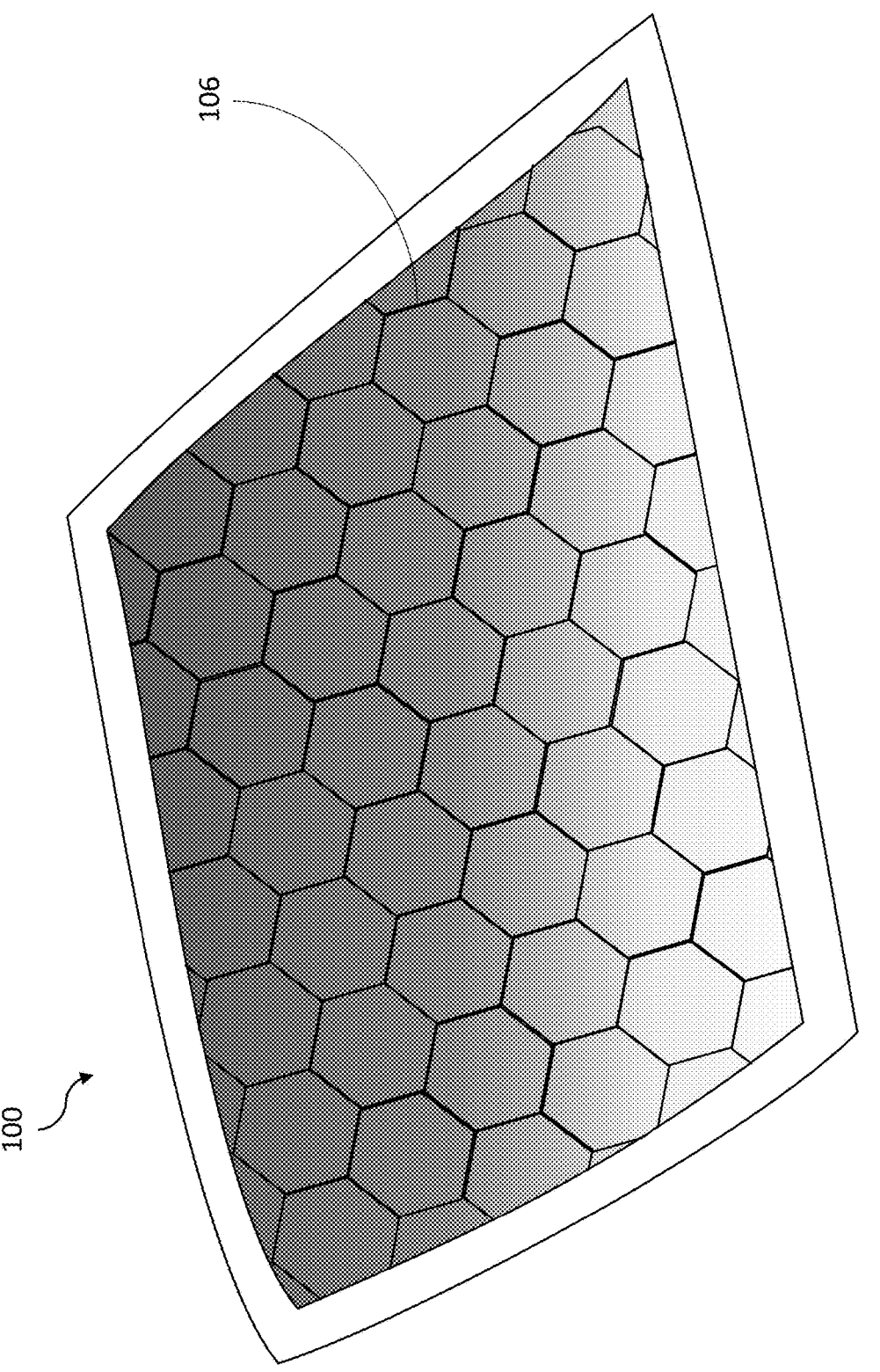
FIG. 2 illustrates a cross-section of an absorbent pad in accordance with an embodiment of the present disclosure.

In various embodiments, as shown in FIG. 2, the absorbent pad 100 includes a fluid volume approximation grid 106 having a plurality of fluid volume estimation regions. In various embodiments, the fluid volume estimation regions each have a particular shape (e.g., circular, hexagonal, square, rectangular, triangular, trapezoidal, quadrilateral, etc.). In various embodiments, the fluid volume approximation grid 106 includes a tessellated pattern. In various embodiments, the fluid volume approximation grid 106 is applied to the outward face of the first sheet of the top layer. In various embodiments, the fluid volume approximation grid 106 is applied to a sheet, said sheet may include any of the visual fluid indicators as described herein, said sheet may then be inserted into any of the layers as described herein. The visual fluid indicator disposed within or on the separate sheet may be any of the dyes herein, such as the disappearing dye, color change dye, or color dye (differentiated by its change to a color from white). The visual fluid indicator and fluid volume approximation grid 106 may be disposed on the same or opposing sides of the separate sheet and inserted into the top layer 102. In various embodiments, the separate sheet may be inserted into any one or more pockets, envelopes, compartments, slots, or other joining mechanisms and/or features with any other portion of the absorbent pad. In various embodiments, each region of the plurality of fluid volume estimation regions demarcates a predetermined amount of fluid (e.g., 50 ml). In various embodiments, a size (e.g., area) of the fluid volume estimation regions may be optimized based on a particular use-case. For example, larger regions corresponding to larger volumes may be used for larger pads. In another example, smaller regions corresponding to smaller volumes may be used where more accurate fluid volume estimates are required. In various embodiments, the fluid volume estimation regions have a constant area across the outward face of the first sheet (e.g., each full hexagon has a same area, and thus equivalent capacity to absorb the bodily fluid). In various embodiments, an angle of each side edge of the particular shape of the fluid volume estimation regions may be maximized so as to mimic a circle. In various embodiments, for tessellation of a pattern, the internal angle of the particular shape may be a factor of 360. For example, some factors of 360 are: 360, 180, and 120, where 360 is a circle, 180 is a straight line, and 120 is a hexagon). In various embodiments, multiple different shapes may be combined in the pattern of the fluid volume estimation regions. For example, pentagons and hexagons may be combined into a tessellated pattern.

In various embodiments, a first portion of the fluid volume estimation regions in the fluid volume approximation grid 106 may include a first area on the outward face of the first sheet and one or more other portions of the fluid volume estimation regions in the fluid volume approximation grid 106 may include a different area on the outward face of the first sheet. For example, fluid volume estimation regions at the center of the absorbent pad may have a larger area (representing a larger fluid volume) than the area of the fluid volume estimation regions radially outward from the center (representing a smaller fluid volume). In another example, fluid volume estimation regions at the center of the absorbent pad may have a smaller area (representing a smaller fluid volume) than the area of the fluid volume estimation regions radially outward from the center (representing a larger fluid volume). In various embodiments, smaller areas of the fluid volume estimation regions may allow for more accurate volume estimation. In various embodiments, the areas of the fluid volume estimation regions may decrease in a radial direction from the center of the absorbent pad. In various embodiments, the areas of the fluid volume estimation regions may increase in a radial direction from the center of the absorbent pad.

In various embodiments, the demarcation of the fluid volume estimation regions may be stamped on the surface of the top layer. In various embodiments, the demarcation of the fluid volume estimation regions may include skin-safe dye applied on to the top surface. In various embodiments, the demarcation of the fluid volume estimation regions may be applied to the first sheet (i.e., the wicking layer) or the second sheet (i.e., the absorbent layer). In various embodiments, the demarcation of the fluid volume estimation regions may be sewn into the top layer, for example, using a nylon and/or hydrophobic material. In various embodiments, to optimize for patient safety, any dye or paint may be non-toxic and any sewing or imprinted material may be flush with the surface to prevent pressure ulcers. In various embodiments, a separate component formed as a sheet in and of itself, the sheet soaked with a visual fluid indicator, such as the dye as described herein, may be inserted into any one of the top layer 102, bottom layer 104, both, and/or a subset thereof.

In various embodiments, when the visual fluid indicator (e.g., a water-soluble dye) on the bottom layer is contacted with the fluid, the visual fluid indicator travels to the outwardly-facing side of the top layer and changes the color of the top layer. Because each fluid volume estimation region in the grid demarcates a specific volume, the number of grid regions having a color change due to the visual fluid indicator may be used to estimate the volume of fluid absorbed by the absorbent pad. In various embodiments, where only a portion of a region has a color change due to the visual fluid indicator, a proportional volume may be used as the approximation. For example, if half of a single hexagonal grid region contains a color change due to the visual fluid indicator and each hexagonal region demarcates 50 ml, then the volume of fluid absorbed by the absorbent pad may be estimated as 25 ml.

In various embodiments, each volume estimation region may demarcate about 5 ml. In various embodiments, each volume estimation region may demarcate about 10 ml. In various embodiments, each volume estimation region may demarcate about 15 ml. In various embodiments, each volume estimation region may demarcate about 20 ml. In various embodiments, each volume estimation region may demarcate about 25 ml. In various embodiments, each volume estimation region may demarcate about 30 ml. In various embodiments, each volume estimation region may demarcate about 35 ml. In various embodiments, each volume estimation region may demarcate about 40 ml. In various embodiments, each volume estimation region may demarcate about 45 ml. In various embodiments, each volume estimation region may demarcate about 50 ml. In various embodiments, each volume estimation region may demarcate about 55 ml. In various embodiments, each volume estimation region may demarcate about 60 ml. In various embodiments, each volume estimation region may demarcate about 65 ml. In various embodiments, each volume estimation region may demarcate about 70 ml. In various embodiments, each volume estimation region may demarcate about 75 ml. In various embodiments, each volume estimation region may demarcate about 80 ml. In various embodiments, each volume estimation region may demarcate about 85 ml. In various embodiments, each volume estimation region may demarcate about 90 ml. In various embodiments, each volume estimation region may demarcate about 95 ml. In various embodiments, each volume estimation region may demarcate about 100 ml. In various embodiments, each volume estimation region may demarcate less than about 50 ml. In various embodiments, each volume estimation region may demarcate more than about 50 ml.

In various embodiments, the bottom layer 104 includes a water-resistant back-sheet. In various embodiments, the bottom layer 104 includes a polymer (e.g., polyethylene, polypropylene). In various embodiments, the bottom layer 104 may provide structural support for the device and prevent fluid contamination on the patient's bed. In various embodiments, the bottom layer 104 allows for visual inspection to confirm the presence of urine at the borders of the bottom layer 104, which may be clear and can appear dry on a traditional pad. In various embodiments, when soiled, a water-soluble dye spreads from the bottom layer 104 into the top layer 102. In various embodiments, the bottom layer 104 is waterproof (e.g., allows no fluid to pass through). In various embodiments, the bottom layer 104 includes a visual fluid indicator 108 disposed thereon. In various embodiments, the visual fluid indicator 108 may include a water-soluble dye. In various embodiments, the visual fluid indicator 108 may be a non-toxic material (e.g., a non-toxic dye). In various embodiments, the visual fluid indicator 108 may indicate (e.g., change color) a pH of the fluid. In various embodiments, the visual fluid indicator 108 may indicate (e.g., change color) the presence of a particular target (e.g., protein, molecule, bacteria, virus, fungus, etc.) in the fluid. In various embodiments, the visual fluid indicator 108 may indicate the lack of a particular target (e.g., protein, molecule, bacteria, virus, fungus, etc.) in the fluid.

In various embodiments, the visual fluid indicator may indicate any off-coloration. For example, an abnormal urine color (abnormal meaning other than clear or yellow) is red, which may be caused by frank hematuria (i.e., blood cells in the urine) or proteins (e.g., hemoglobin or myoglobin). In various embodiments, a visual indicator (e.g., a dye) may be a particular color, such as yellow, and when it contacts red fluid it will turn orange as opposed to the dye turning a darker color or having subtle color changes with normal colors of urine. In various embodiments, where the visual indicator (e.g., dye) is added to the bottom sheet allows an unused pad to appear white like any other pad, but when urinated, the volume of the urine will change color based on the visual indicator. In various embodiments, this color change generates a clearly defined, demarcated border for the healthcare professional to be able to count the number of saturated regions. In various embodiments, the visual indicator (e.g., a dye) may be a first color prior to contact with a fluid and a second color after contact with a fluid. For example, the visual indicator may start black and appear white after contact, thereby acting as "disappearing dye" to indicate fluid contact. In various embodiments, the visual indicator may undergo a color change before and after contact with fluid, including a specific color change based on the fluid contacted by the visual fluid indicator. The visual indicator may be white prior to contact with the fluid and change to a color that emphasizes the color of the fluid with which it contacts, for example it may change red to indicate blood in a patient's urine.

As shown in FIG. 1 by arrow 110a, the fluid 112 (e.g., urine) contacts the first sheet 102a of the top layer 102 and is wicked across (e.g., spread approximately evenly) the first sheet 102a. The fluid 112 passes through the first layer 102a and is absorbed by the absorbent second sheet 102b (which may include an absorbent material, such as a super absorbent polymer). After being absorbed by the second sheet 102b, the fluid 112 contacts the visual fluid indicator 108 (e.g., a water-soluble dye) disposed on the bottom sheet 104 thereby dissolving the visual fluid indicator 108 and, as indicated by arrow 110b, allowing the visual fluid indicator 108 to diffuse through the second 102b and first 102a sheets of the top layer 102. The visual fluid indicator 108 changes the color of the top layer 102 such that a healthcare professional may use the fluid volume approximation grid to approximate the volume of fluid output of the patient. Because the visual fluid indicator permanently marks the extent of fluid absorbed by the absorbent pad, the absorbent pad thus allows healthcare professionals to estimate the volume of fluid output of a patient even if a portion of the absorbent pad dries during use. In various embodiments, the visual fluid indicator is disposed within at least a portion of the bottom layer 104. In various embodiments, the visual fluid indicator is disposed within at least a portion of the top layer 102. In various embodiments, a separate component formed as a sheet soaked or otherwise treated with a visual fluid indicator, such as the dye as described herein, may be inserted into any one of the top layer 102, bottom layer 104, both, and/or a subset thereof.

In various embodiments, the absorbent pad 100 includes a discrete top layer 102 and bottom layer 104 attached to one another during manufacture. In various embodiments, the layers may be laminated together using various methods. In various embodiments, the layers may be attached via an adhesive (e.g., acrylic bonded). In various embodiments, the layers may be attached along a strip having a predetermine width around the perimeter of the absorbent pad 100. In various embodiments, the layers may be bonded together using heat. In various embodiments, the layers may be press fit together. In various embodiments, the layers may be mechanically fastened together, such as with a textile fastener such as yarn, thread, silk, or other fibrous methods stitched or woven between the layers as necessary. In various embodiments the layers may be stapled together.

In various embodiments, any of the layers may be manufactured as a woven sheet. In various embodiments, any of the layers may be manufactured as a non-woven sheet. In various embodiments, the layers may be manufactured via melt-blowing. In various embodiments, any of the layers may include one or more layers having a plurality of randomly-oriented fibers (e.g., cotton fibers). In various embodiments, any of the layers may include one or more layers having a plurality of fibers oriented in one or more pre-determined directions (e.g., unidirectional, bidirectional, 30-60-30, 45-45, etc.).

Figure 3A:
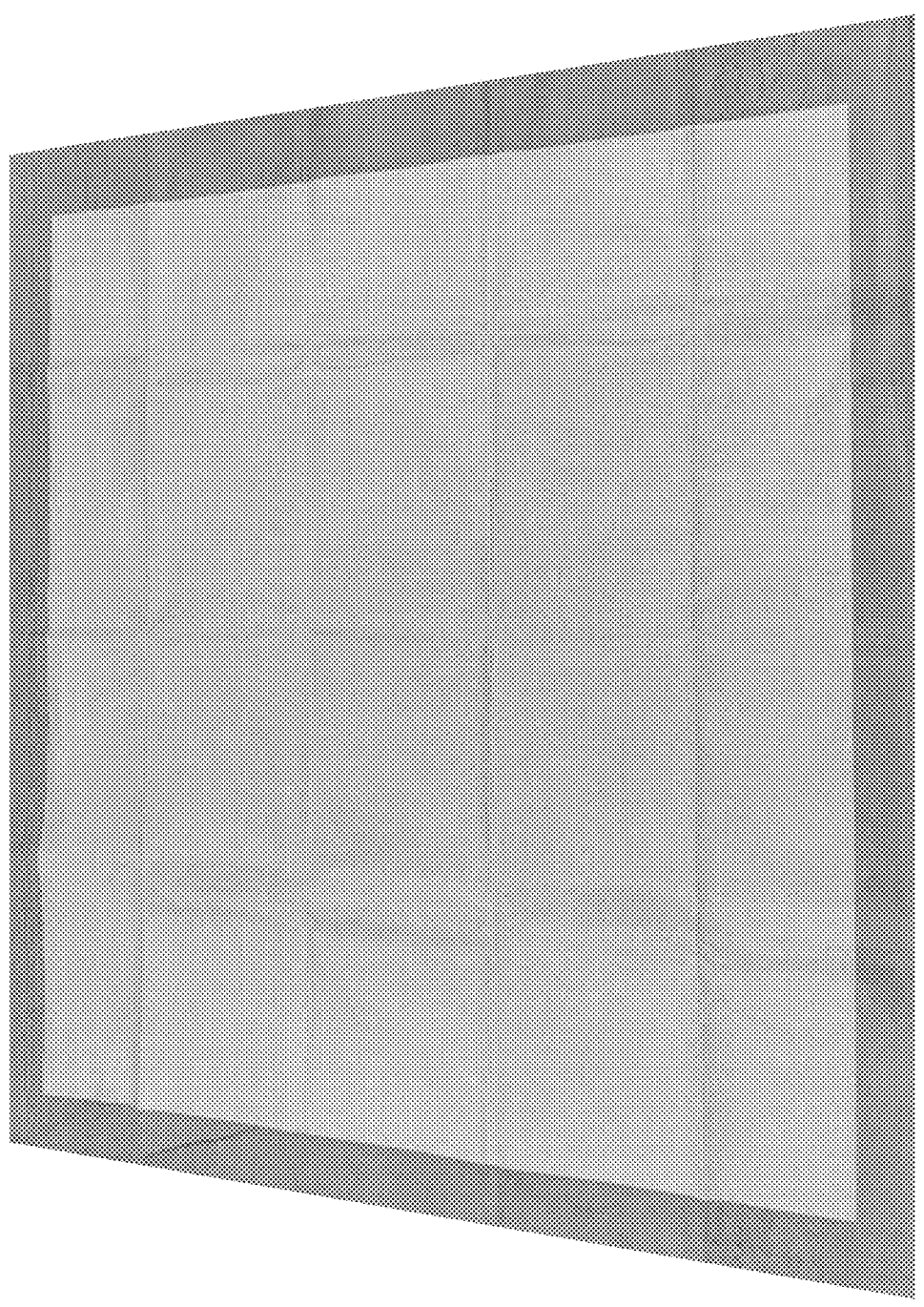
FIGS. 3A-3F illustrate a method of manufacturing an absorbent pad in accordance with an embodiment of the present disclosure.
Figure 3B:
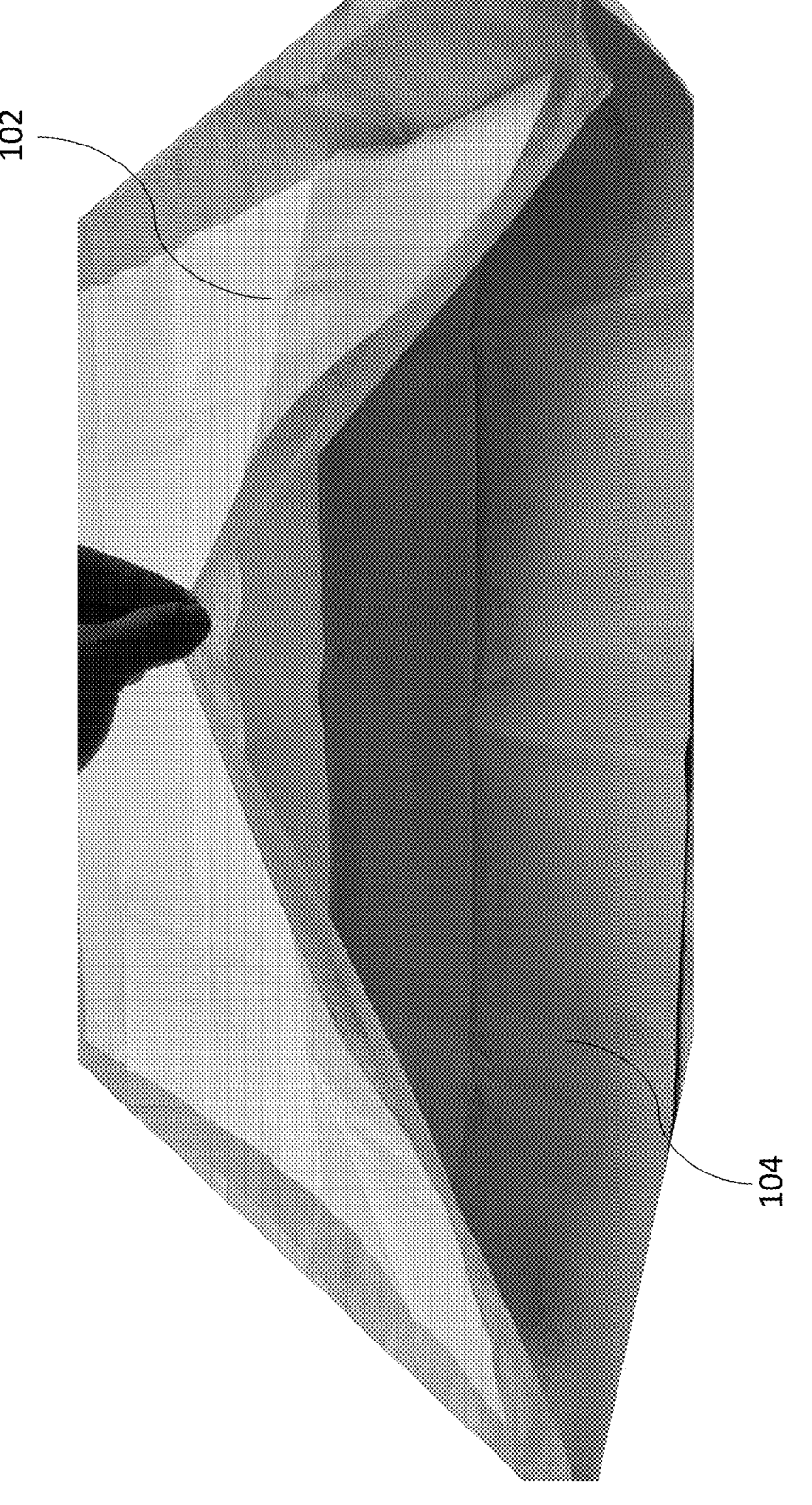
Figure 3C:
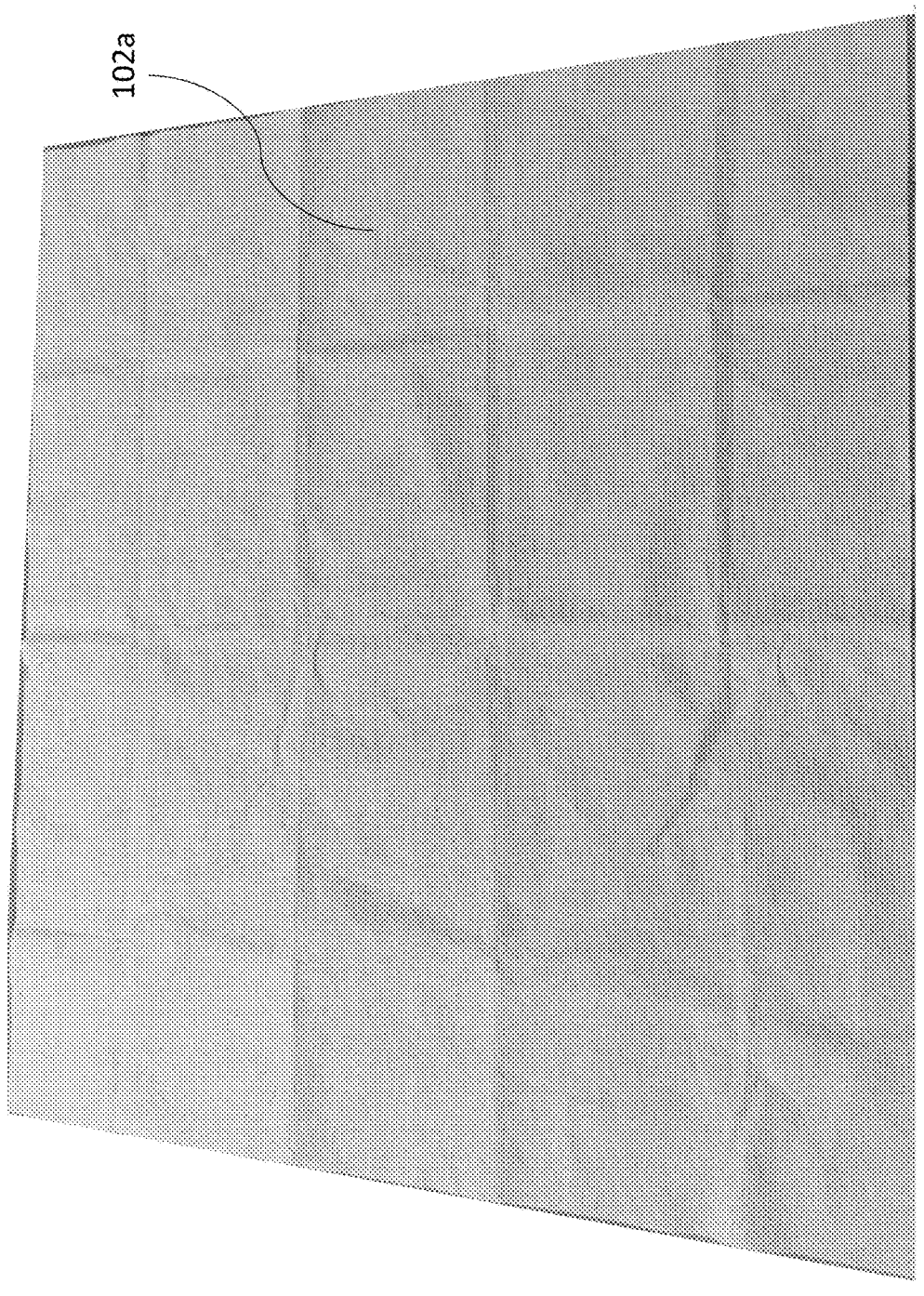
Figure 3D:
Figure 3E:
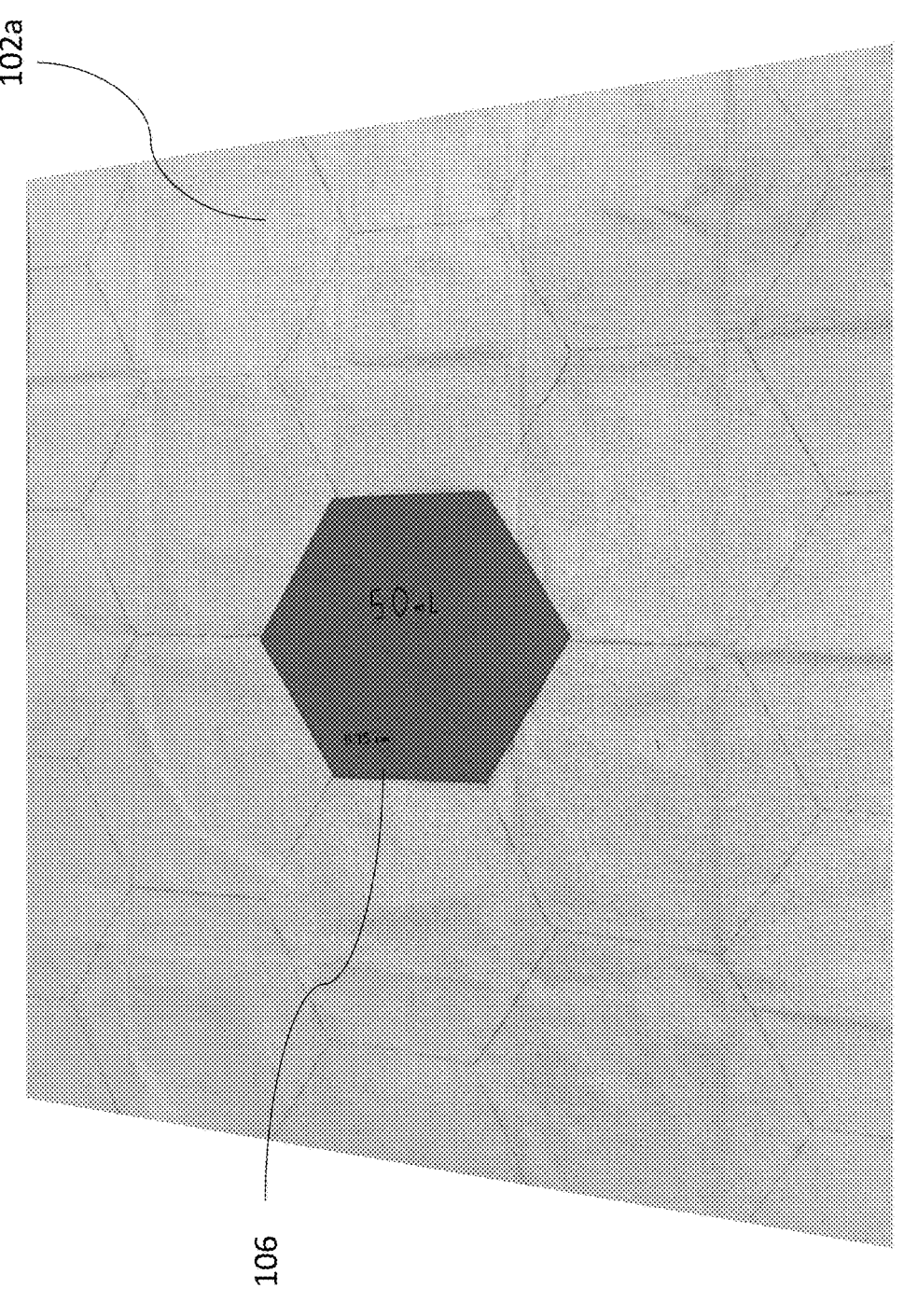
Figure 3F:
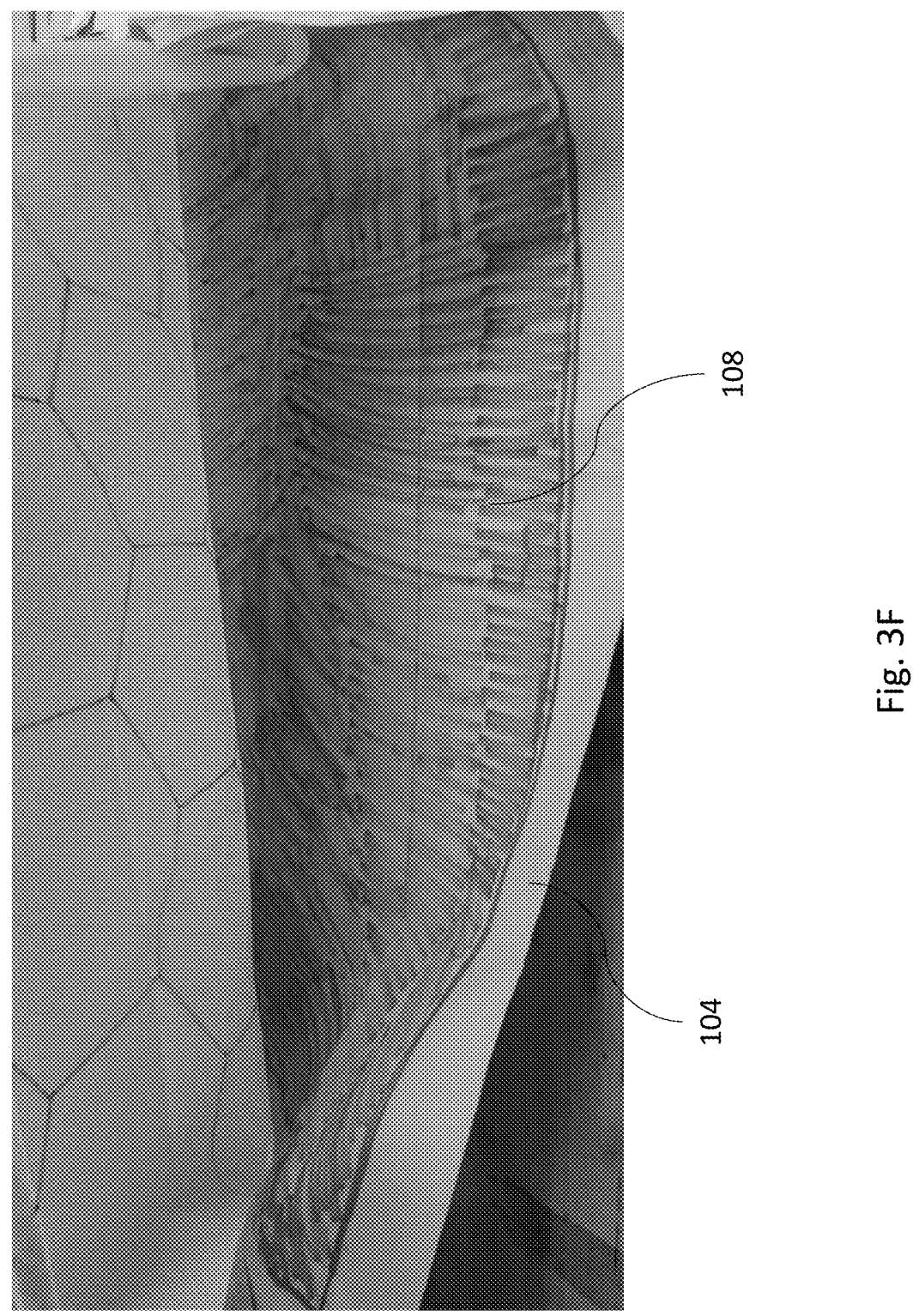

FIG. 3A-3F illustrate a method of manufacturing an absorbent pad. FIG. 3A illustrates a pre-manufactured absorbent pad. As shown in FIG. 3B, the top layer 102 and bottom layer 104 are separated from one another. As shown in FIGS. 3C-3D, the top layer is further divided into two sublayers—a first sheet 102a (wicking sheet) that is configured to allow for the fluid to spread evenly before absorption into the other sublayer and a second sheet 102b that contains a super absorbent polymer (i.e., sodium polyacrylate, potassium polyacrylate, etc.). As shown in FIG. 3E, a predetermined pattern (e.g., hexagonal) is tessellated on the first sheet 102a of the top layer 102. A shown in FIG. 3F, a water-soluble, non-toxic dye is distributed on the inward facing surface of the bottom layer 104. As described above, the bottom layer 104 may be a plastic polymer (e.g., polypropylene) and the dye may diffuse to the upper layer(s), such as the absorbent layer and wicking layer, once the dye contacts the fluid and is wetted.

Figure 4:
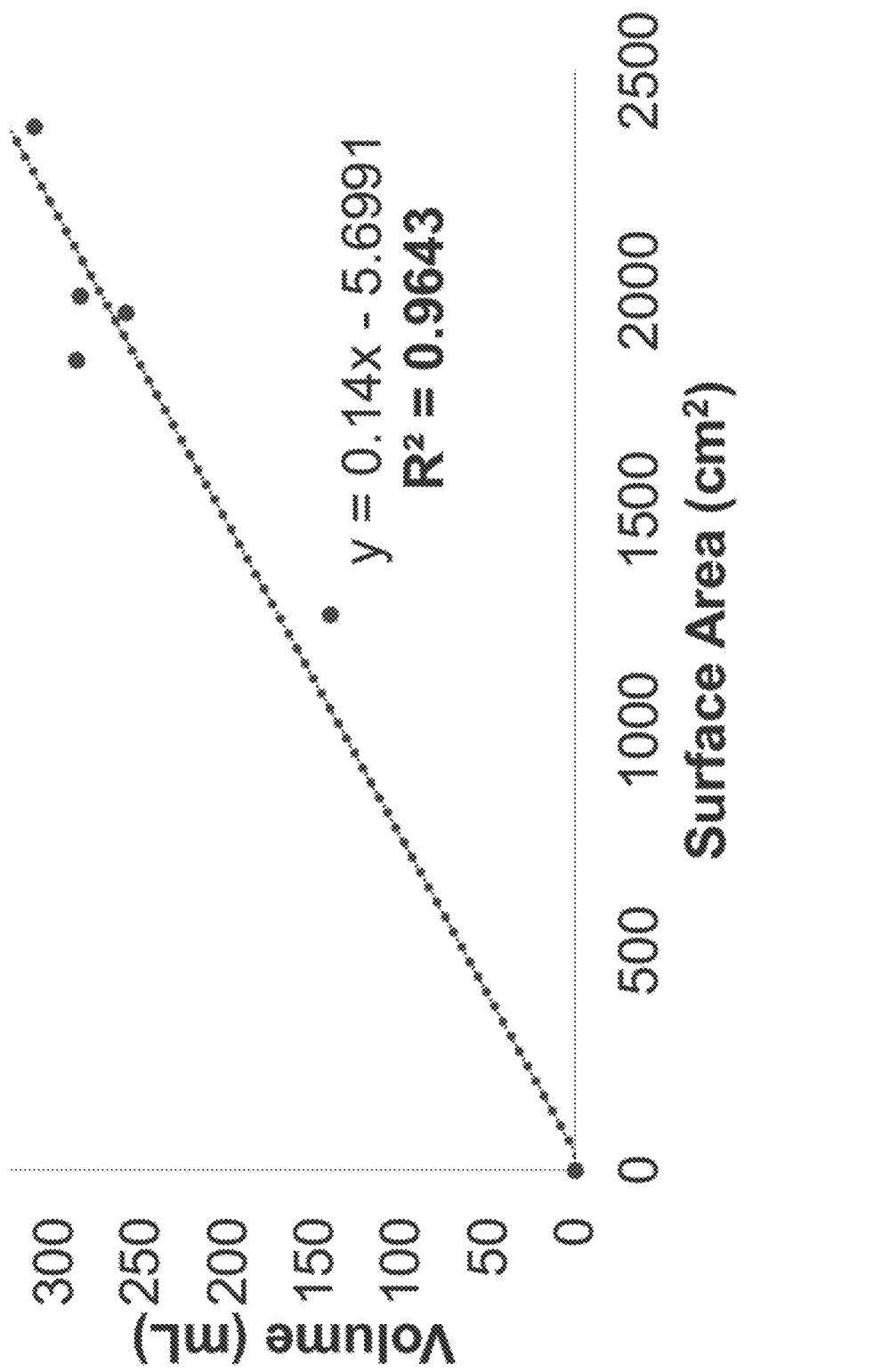
FIG. 4 illustrates an absorbent pad after use in accordance with an embodiment of the present disclosure.

FIG. 4 illustrates a graph of surface area to volume correlation. As shown in FIG. 4, as the surface area (cm²) of the absorbent pad increases, the volume (ml) of fluid absorbed increases linearly.

In various embodiments, a maximum volume of urine that an absorbent pad can absorb under a patient's weight is 941 ml+/−114 ml. In various embodiments, a maximum volume of a normal human bladder is about 500 ml, which means that the absorbent pad has a factor of safety of two.

EXAMPLE

Figure 5:
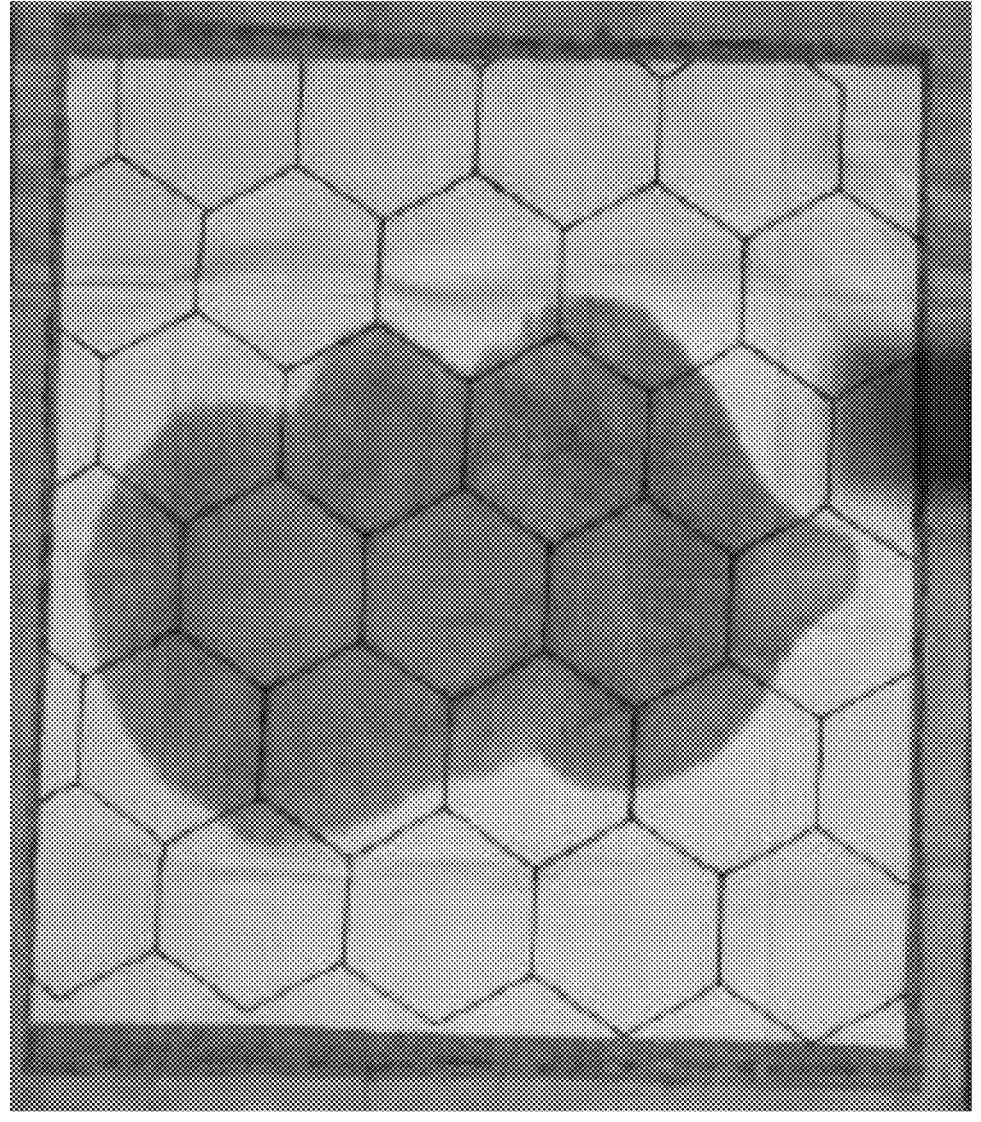
FIG. 5 illustrates a graph of surface area to volume correlation in accordance with an embodiment of the present disclosure.

A pad is positioned under a patient on a hospital bed. When the patient urinates on the pad, as shown in FIG. 5, urine will first spread across the wicking layer (first sheet of the top layer) and then quickly be absorbed by the sodium polyacrylate (second sheet of the top layer). The urine will also wet the dye disposed on the bottom layer, allowing the dye to diffuse to the top of the absorbent pad. This will result in a color change in the section of the pad that is wet, thereby providing a visual fluid indicator of wetness, even after at least a portion of the pad dries. Due to wicking sublayer, the surface area of the wet section is approximately proportional to the volume of the fluid. Each hexagon in the fluid volume approximation grid that changes color due to the dye represents a pre-determined amount (e.g., 50 ml) of absorbed urine. Clinicians can proceed to count the number of soaked hexagons while they are rolling the pad out from under the patient to estimate a volume of urine excreted. This allows for smooth integration into existing workflow and allows for quick volume estimation that may be used in clinical decision-making.

While the disclosed subject matter is described herein in terms of certain preferred embodiments, those skilled in the art will recognize that various modifications and improvements may be made to the disclosed subject matter without departing from the scope thereof. Moreover, although individual features of one embodiment of the disclosed subject matter may be discussed herein or shown in the drawings of the one embodiment and not in other embodiments, it should be apparent that individual features of one embodiment may be combined with one or more features of another embodiment or features from a plurality of embodiments.

In addition to the specific embodiments claimed below, the disclosed subject matter is also directed to other embodiments having any other possible combination of the dependent features claimed below and those disclosed above. As such, the particular features presented in the dependent claims and disclosed above can be combined with each other in other manners within the scope of the disclosed subject matter such that the disclosed subject matter should be recognized as also specifically directed to other embodiments having any other possible combinations. Thus, the foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the method and system of the disclosed subject matter without departing from the spirit or scope of the disclosed subject matter. Thus, it is intended that the disclosed subject matter include modifications and variations that are within the scope of the appended claims and their equivalents.

What is claimed is:

1. An absorbent pad comprising:
a top layer comprising:
  a first sheet, the first sheet comprising:
    an outward face and an inward face, wherein the first sheet comprises a wicking material, the first sheet further comprising a volume approximation grid having a plurality of fluid volume estimation regions, wherein at least one fluid volume estimation region is encircled by a subset of adjacent fluid volume estimation regions, each of which is contiguous with the at least one fluid volume estimation region along a portion of a perimeter of the at least one fluid volume estimation region; and
  a second sheet, the second sheet comprising an absorbent material;
  the second sheet attached to the inward face of the first sheet; and
a bottom layer comprising an outward face and an inward face, the inward face of the bottom layer attached to the second sheet; and
a visual fluid indicator disposed on at least a portion of the bottom layer, wherein the visual fluid indicator is configured to migrate to the first sheet and produce a visible color change on the outward face of the first sheet.

2. The absorbent pad of claim 1, wherein the visual fluid indicator comprises a dye indicating a pH of the fluid.

3. The absorbent pad of claim 1, wherein the visual fluid indicator contacts with the second sheet.

4. The absorbent pad of claim 2, wherein the dye comprises material properties such that, when in contact with a fluid, the fluid dissolves the dye and the dye diffuses from the inward face of the bottom layer to the outward face of the first sheet to thereby indicate the presence of the fluid.

5. The absorbent pad of claim 1, wherein the wicking material comprises material properties that allow the fluid to spread across the first sheet.

6. The absorbent pad of claim 1, wherein the absorbent material comprises an absorbent polymer.

7. The absorbent pad of claim 6, wherein the absorbent polymer comprises sodium polyacrylate.

8. The absorbent pad of claim 1, wherein the bottom layer comprises a waterproof material.

9. The absorbent pad of claim 1, wherein the bottom layer comprises a polymer.

10. The absorbent pad of claim 9, wherein the polymer comprises polypropylene.

11. The absorbent pad of claim 1, wherein the plurality of fluid volume estimation regions are formed on the outward face of the first sheet.

12. The absorbent pad of claim 1, wherein each of the plurality of fluid volume estimation regions comprises an equal surface area on the first sheet.

13. The absorbent pad of claim 1, wherein a first portion of the plurality of fluid volume estimation regions comprises a first area on the outward face of the first sheet and a second portion of the plurality of fluid volume estimation regions comprises a second area.

14. The absorbent pad of claim 1, wherein each of the plurality of volume estimation regions comprise a hexagonal shape.

15. The absorbent pad of claim 1, wherein the first sheet comprises a non-woven fabric.

16. The absorbent pad of claim 1, wherein the second sheet comprises a non-woven fabric.

17. The absorbent pad of claim 1, wherein the visual fluid indicator and the volume approximation grid are formed on a separate sheet, the separate sheet removably fixed to at least a portion of the top layer or bottom layer.

18. A method of detecting the presence of and approximating a volume of a fluid, the method comprising:
  providing an absorbent pad, the absorbent pad comprising:
    a top layer comprising a first sheet, the first sheet comprising:
      an outward face and an inward face, wherein the first sheet comprises a wicking material, the first sheet further comprising a volume approximation grid having a plurality of fluid volume estimation regions, wherein at least one fluid volume estimation region is encircled by a subset of adjacent fluid volume estimation regions, each of which is contiguous with the at least one fluid volume estimation region along a portion of a perimeter of the at least one fluid volume estimation region; and
    a second sheet, the second sheet comprising an absorbent material, the second sheet attached to the inward face of the first sheet; and
    a bottom layer comprising an outward face and an inward face, the inward face of the bottom layer attached to the second sheet; and
    a visual fluid indicator disposed on at least a portion of the bottom layer, wherein the visual fluid indicator is configured to migrate to the first sheet and produce a visible color change on the outward face of the first sheet;

contacting the absorbent pad with the fluid; and
  determining a number of regions on the first sheet having the fluid thereon.

19. A method of manufacturing an absorbent pad, the method comprising:
  providing a top layer comprising a first sheet and a second sheet, the first sheet having an outward face and an inward face,
    the second sheet attached to the inward face of the first sheet, wherein the first sheet comprises a wicking material, wherein the second sheet comprises an absorbent material;
  providing a bottom layer comprising an outward face and an inward face;
  forming a volume approximation grid having a plurality of fluid volume estimation regions on at least a portion of the first sheet, wherein at least one fluid volume estimation region is encircled by a subset of adjacent fluid volume estimation regions, each of which is contiguous with the at least one fluid volume estimation region along a portion of a perimeter of the at least one fluid volume estimation region;
  applying a visual fluid indicator on the bottom layer, wherein the visual fluid indicator is configured to migrate to the first sheet and produce a visible color change on the outward face of the first sheet; and
  affixing the bottom layer having the visual fluid indicator applied thereon to the top layer.

20. The method of claim 19, wherein the visual fluid indicator is applied to a face of the bottom layer that contacts the second sheet.

* * * * *